United States Patent [19]

Markley

[11] 4,133,837
[45] Jan. 9, 1979

[54] PREFERENTIAL ALIPHATIC HALOGENATION OF AR-SUBSTITUTED ALKYLBENZENES

[75] Inventor: Lowell D. Markley, Midland, Mich.

[73] Assignee: The Dow Chemical Company, Midland, Mich.

[21] Appl. No.: 852,409

[22] Filed: Nov. 17, 1977

Related U.S. Application Data

[63] Continuation-in-part of Ser. No. 738,401, Nov. 3, 1976, Pat. No. 4,087,473.

[51] Int. Cl.² .............................................. C07C 25/14
[52] U.S. Cl. ................................................. 260/651 R
[58] Field of Search .................................... 260/651 R

[56] References Cited

U.S. PATENT DOCUMENTS

| | | | |
|---|---|---|---|
| 2,193,823 | 3/1940 | Levine et al. | 260/650 R |
| 2,265,312 | 12/1941 | Quattlebaum et al. | 260/650 R |
| 2,432,737 | 12/1947 | Erickson et al. | 260/650 R |
| 3,190,825 | 6/1965 | Huyser | 260/651 R |
| 3,553,274 | 1/1971 | Lewis et al. | 260/650 R |

FOREIGN PATENT DOCUMENTS

| | | | |
|---|---|---|---|
| 669800 | 9/1963 | Canada | 260/651 R |
| 2604276 | 5/1976 | Fed. Rep. of Germany | 260/651 R |
| 4327212 | 11/1968 | Japan | 260/651 R |

Primary Examiner—O. R. Vertiz
Assistant Examiner—Wayne A. Langel
Attorney, Agent, or Firm—P. D. Shepherd

[57] ABSTRACT

In an isomeric mixture of ar-substituted-1-(sec-alkyl)-benzenes, such as a mixture of 2-chlorocumene, 3-chlorocumene and 4-chlorocumene, the alkyl groups of the 3-isomer and 4-isomer react preferentially with a halogen in the presence of a catalyst such as benzoyl peroxide to form a 3-halo-1-($\alpha$-alkyl, $\alpha$-halo)alkylbenzene and 4-halo-1-($\alpha$-alkyl, $\alpha$-halo)alkylbenzene such as 3-chloro-$\alpha$-bromocumene, and 4-chloro-$\alpha$-bromocumene.

10 Claims, No Drawings

PREFERENTIAL ALIPHATIC HALOGENATION OF AR-SUBSTITUTED ALKYLBENZENES

CROSS-REFERENCE TO RELATED APPLICATION

This application is a continuation-in-part of application Ser. No. 738,401 filed Nov. 3, 1976, now U.S. Pat. No. 4,087,473.

BACKGROUND OF THE INVENTION

The invention relates to processes for the preparation of ar-substituted alkylbenzenes and to a process for the preferential aliphatic halogenation of at least one isomer in an isomeric mixture of ar-substituted alkylbenzenes.

It is known in the art that 2,4-dihalo-1-alkylbenzenes can be isomerized to 3,5-dihalo-1-alkylbenzenes in the presence of a catalyst containing aluminum and bromine. See, for example, U.S. Pat. No. 3,553,274.

It is also known in the art that aliphatic (side chain) halogenation of, among other isomers, the ar,ar-dihaloethylbenzenes can be catalyzed by phosphorus trihalide or phosphorus pentahalide. Such reactions are typically conducted in the liquid phase at a temperature of between about 40° C. and about 80° C. U.S. Pat. No. 2,265,312 teaches that the above-mentioned catalysts are useful in carrying out such aliphatic halogenation reactions.

In U.S. Pat. No. 2,432,737, a method is taught for the production of a mixture of ring isomers of dichlorostyrene. Both $\alpha$-chlorination and $\beta$-chlorination of the side chains of a mixture of ethyldichlorobenzene isomers result under the conditions of the process which are the bubbling of liquid chlorine through the mixture of isomers at a temperature of about 40° C. to 80° C. in the presence of a catalyst such as $PCl_3$.

In U.S. Pat. No. 2,193,823, a method is taught for selective $\alpha$-chlorination of an ethyl side chain of an ar-halo-ar-ethylbenzene. For example, this patent describes chlorinating the $\alpha$-carbon of ethylpentachlorobenzene by contacting the same in the liquid phase with chlorine gas in the presence of the light of an ordinary electric light bulb to produce $\alpha$-chloroethylpentachlorobenzene.

Heretofore, the preferential aliphatic halogenation of one or more isomers in a mixture of ar-substituted alkylbenzenes has not been disclosed.

SUMMARY OF THE INVENTION

The present invention is a process for the preferential, aliphatic halogenation of a 3-substituted-1-(sec-alkyl) benzene isomer and a 4-substituted-1-(sec-alkyl) benzene isomer present in an isomeric mixture of mono-substituted-1-(sec-alkyl) benzenes. One isomer that is preferentially halogenated has a substituent in the 3-ring position (hereinafter called 3-isomer). The other isomer that is preferentially halogenated has a substituent in the 4-ring position (hereinafter called 4-isomer). The remaining isomer(s) which is not halogenated in the process is a 2-substituted-1-(sec-alkyl) benzene (hereinafter called 2-isomer).

The process comprises contacting the isomeric mixture with a suitable halogen in the presence of an amount of a free radical generator and under conditions sufficient to preferentially halogenate the 3-isomer and 4-isomer in the alpha position of the sec-alkyl substituent. The alpha position of the sec-alkyl substituent is on the carbon bonded to the benzene ring. This preferential halogenation is surprising in that it occurs only at the alpha position of essentially all of the 3-isomer and the 4-isomer while essentially none of the 2-isomer(s) is halogenated. Thus, the product of the preferential, aliphatic halogenation reaction is a mixture comprising the $\alpha$-halogenated 3-isomer, the $\alpha$-halogenated 4-isomer and the 2-isomer. The halogenated products of this process are useful as intermediates in the synthesis of useful organic compounds.

Of particular interest in the practice of this invention is a process for the preferential, aliphatic halogenation of the 4-isomer in an isomeric mixture containing the 4-isomer and the 2-isomer but containing no 3-isomer. The $\alpha$-halogenated 4-isomer and/or $\alpha$-halogenated 3-isomer of this process are readily separated from the 2-isomer. The $\alpha$-halogenated isomers are useful as intermediates in the manufacture of herbicides.

DETAILED DESCRIPTION OF THE EMBODIMENTS

In the practice of the present invention it is essential to employ: an isomeric mixture, a halogenating agent, and a free radical generator. A solvent is optionally employed.

Isomeric mixtures of particular interest contain a 2-substituted-1-(sec-alkyl) benzene of structure (I), a 4-substituted-1-(sec-alkyl) benzene of structure (III) and optionally a 3-substituted-1-(sec-alkyl) benzene of structure (II).

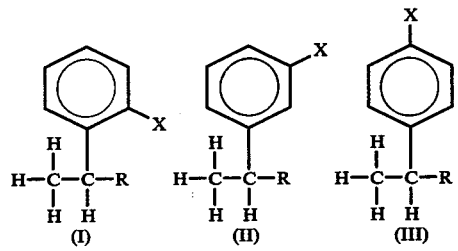

In structures (I), (II) and (III), each X is independently methyl, chloro, bromo, fluoro, $-CF_3$ or $-CCl_3$. Preferably, each X is chloro, bromo, or fluoro. Most preferably, each X is chloro. The R of structures (I), (II) and (III) is a straight- or branched-chain alkyl group having from 1 to 6 carbon atoms, preferably from 1 to 3 carbon atoms. Mixtures of isomers represented by the formulas (I), (III) and optionally (II) wherein R is methyl and X is independently chloro, bromo or fluoro are preferred for use in the present invention.

The isomeric mixtures of particular interest can be prepared in any number of ways. One method consists of reacting a suitable substituted benzene with a suitable alkylating agent such as alkyl halides, olefins and alkyl alcohols in the presence of a Friedel-Crafts catalyst such as aluminum trichloride and an acid. The product of the reaction step is a mixture containing substantial amounts of 2-isomer, 3-isomer, and 4-isomer.

The halogenating agent is advantageously a halogen such as bromine and iodine with bromine being the most preferred. Chlorine halogenating agents, however, are not operable in the present invention. A suitable halogen or any agent that is capable of generating the suitable halogen atom can be used, such as a suitable halogen-containing solid or liquid, or a compound such as N-bromo-acetamide or N-bromo-succinimide. Suitable halogens are preferably supplied at a ratio of about one mole of halogen atoms per mole of combined 3-isomer and 4-isomer. While excess halogenating agent can be employed, too large an excess may lead to some halogenation of the 2-isomer.

Suitable free radical generators include ultraviolet light and/or a catalyst capable of supplying free oxygen atoms such as a peroxide. In the case of a peroxide, a quantity is used sufficient to cause halogenation of the 3-isomer and/or 4-isomer. If a peroxide such as benzoyl peroxide is used, it is conveniently added to the isomeric mixture along with the optional solvent. With a peroxide, an amount sufficient to cause halogenation of the 3-isomer and/or 4-isomer is typically between about 1 percent and about 5 percent based upon the weight of the isomeric mixture, and preferably between about 2.5 percent and about 4.0 percent based upon the weight of the isomeric mixture.

Generally, a solvent, such as benzene or carbon tetrachloride, is used in the preferential, aliphatic halogenation, although the reaction can be conducted neat if desired. If used, the solvent is most advantageously employed in an amount between about 1 and about 2 grams of solvent per gram of isomeric mixture.

The preferential, aliphatic halogenation step is advantageously conducted in the liquid phase at a temperature of between about 0° C. and about 90° C., and preferably between about 10° C. and about 35° C. The halogenation step is typically conducted in the presence of mild agitation sufficient to maintain an essentially homogeneous mixture of the reactants.

In conducting the halogenation step, neither the rate of halogen addition nor the order of addition of the reactants is critical provided that at any time during the reaction, no more than about one mole of halogenating agent is present for one mole of combined unreacted 3-isomer and 4-isomer. Preferably, the suitable halogen is added in liquid form to the other reagents. In the usual case the isomeric mixture and catalyst are mixed homogeneously before halogen addition is begun. A typical halogenation step generally requires from about 1 hour to about 15 hours.

The preferential, aliphatic halogenation of isomeric mixtures of particular interest yield mixtures comprising unreacted 2-isomer (structure I), α-halogenated 4-isomer (structure V) and when the unreacted 3-isomer is present in the unreacted isomeric mixture, α-halogenated 3-isomer (structure IV).

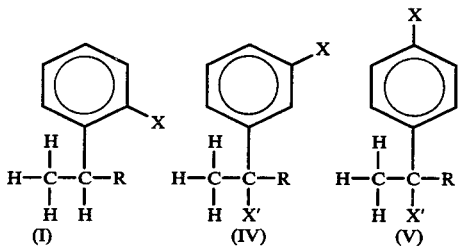

wherein X and R are as above defined and X' is bromo or iodo. Compounds of structures (IV) and (V) are separable from the compound of structure (I) by distillation.

The following example is given to illustrate the invention and should not be construed as limiting its scope. All percentages in the example are by weight unless otherwise indicated.

EXAMPLE

In a 2 liter vessel equipped with a stirring means and a heating means, a mixture is formed by stirring at room temperature 151 g of chlorobenzene and 154 g (1 mole) of a mixture composed of 64 percent 3-chlorocumene, 11 percent 4-chlorocumene and 25 percent 2-chlorocumene. The mixture is heated to 14° C. and held at that temperature while halogenation with 121 g (about 0.75 mole) of bromine is conducted over a 4-hour period in the presence of ultraviolet light. The mixture is stirred and maintained at 14° C. as addition of bromine creates a crude product mixture.

The HBr formed during the reaction is driven off by sparging the crude product mixture for about 40 minutes with a moderate flow of nitrogen gas. Then, the crude product mixture is heated under vacuum to remove the chlorobenzene yielding 213 g of a product mixture containing 72 percent 3-chloro-α-bromocumene and 4-chloro-α-bromocumene, 25 percent of unreacted 2-chlorocumene and 3 percent of 3-chlorocumene and 4-chlorocumene.

Similar results were achieved when the foregoing example was carried out using other free radical generators such as t-butyl perbenzoate or azobisisobutyronitrile.

What is claimed is:

1. A process for preferential, aliphatic bromination of compounds of structure (II) and structure (III) in an isomeric mixture of a compound of structure (I) and the compounds of structure (II) and structure (III);

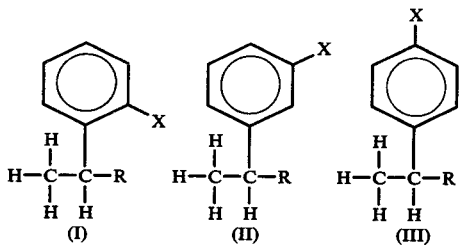

wherein each X is individually methyl, chloro, bromo, fluoro, —$CF_3$ or —$CCl_3$; R is an alkyl group containing from about 1 to about 6 carbon atoms; said process comprising the step of contacting the mixture with a brominating agent in the presence of an amount of a free radical generator and under conditions sufficient to cause bromination of the compounds of structure (II) and structure (III) in the alpha position of the 1-sec-alkyl group whereby essentially none of the compound of structure (I) is brominated.

2. The process of claim 1 wherein the free radical generator is ultraviolet light.

3. The process of claim 1 wherein the brominating agent with which the mixture is contacted is bromine.

4. The process of claim 1 wherein R is methyl.

5. The process of claim 1 wherein X is chlorine.

6. The process of claim 1 conducted at a temperature of between about 0 and about 90° C.

7. The process of claim 1 wherein X is chlorine, R is methyl, the free radical generator is utlraviolet light conducted at a temperature of between about 10 and 35° C.

8. The process of claim 1 further comprising a step of separating the brominated compounds of structures (II) and (III) from the resulting mixture of the brominated compounds of structures (II) and (III) and the compound of structure (I).

9. A process for preferential, aliphatic bromination or iodination of a 4-substituted-1-(sec-alkyl)benzene in an isomeric mixture containing (1) a 4-substituted-1-(sec-alkyl)benzene and (2) a 2-substituted-1-(sec-alkyl)benzene, said process comprising the step of contacting the mixture with a suitable brominating or iodinating agent in the presence of an amount of a free radical generator and under conditions sufficient to cause bromination or iodination of the 4-isomer in the alpha position of the 1-sec-alkyl group, whereby essentially none of the 2-isomer is brominated or iodinated.

10. The process of claim 9 wherein the isomeric mixture also contains a 3-substituted-1-(sec-alkyl)benzene which is also preferentially brominated or iodinated in the alpha position of the 1-sec-alkyl group.